United States Patent [19]

Thunberg et al.

[11] Patent Number: 5,011,968
[45] Date of Patent: Apr. 30, 1991

[54] PROCESS FOR THE PREPARATION OF 3-CYANO-3,5,5-TRIMETHYLCYCLOHEXANONE

[75] Inventors: Jon C. Thunberg, Milford, N.H.; Walter B. Begonis, Reading, Mass.

[73] Assignee: W. R. Grace & Co.-Conn., New York, N.Y.

[21] Appl. No.: 475,051

[22] Filed: Feb. 6, 1990

[51] Int. Cl.$^5$ .......................................... C07C 253/10
[52] U.S. Cl. ...................................... 558/341; 558/431
[58] Field of Search ................................ 558/431, 341

[56] References Cited

U.S. PATENT DOCUMENTS 4,299,775  11/1981  Dubreux ........................ 558/431 X

FOREIGN PATENT DOCUMENTS 275204   4/1964  Australia .
0028179  5/1981  European Pat. Off. .
1240854  5/1967  Fed. Rep. of Germany .
1452374  9/1966  France .
116038   7/1982  Japan .

OTHER PUBLICATIONS

Chemical Abstracts 60:11885e (1964), Musker.
Chemical Abstracts 103:75809z (1985), Sumitomo.

*Primary Examiner*—Joseph Paul Brust
*Attorney, Agent, or Firm*—Kevin S. Lemack; William L. Baker

[57] ABSTRACT

A process for preparing isophorone nitrile is disclosed, whereby isophorone is reacted with hydrogen cyanide in the presence of a quaternary ammonium catalyst. Remaining catalyst is removed by thermal destruction and nitrogen sparging. Residual cyanide is removed by acidification and nitrogen sparging.

17 Claims, 2 Drawing Sheets

PROCESS FOR THE PREPARATION OF 3-CYANO-3,5,5-TRIMETHYLCYCLOHEXANONE

BACKGROUND OF THE INVENTION

Isophorone nitrile (IPN) or 3-cyano-3,5,5-trimethylcyclohexanone is a critical intermediate in the synthetic scheme to the diisocyanate (IPDI). Numerous prior art processes have been developed to synthesize IPN. For example, Dubreux U.S. Pat. No. 4,299,775 discloses a two-phase process for the preparation of IPN by reacting isophorone (IPH) with a cyanide in the presence of a catalytic amount of a phase-transfer agent. The quaternary ammonium catalysts are used as their chloride or bromide-salts; the chloride or bromide ion is exchanged for cyanide ion and in this cyanide form is transferred from the water to the solvent layer via the well known phase transfer mechanism. German Patent No. 1,240,854 to Scholven-Chemie discloses a process for the preparation of IPN by reacting isophorone with hydrogen cyanide in the presence of a basic catalyst such as alkali cyanide, hydroxides or alcoholates. The catalyst is removed by washing with dilute nitric acid.

Japanese Laid-Open specification 61-33157 to Nippon Kagako K.K. discloses a process for the preparation of isophorone nitrile by reacting isophorone with hydrogen cyanide in the presence of tetra-n-butylammonium hydroxide, tetra-n-butylphosphonium hydroxide or benzyltrimethylammonium hydroxide. The resulting reaction liquid is washed in water.

Acidic washing to remove catalyst produces an aqueous effluent saturated in isophorone and containing some cyanide. Disposal of such an effluent adds significantly to the cost of the product.

SUMMARY OF THE INVENTION

The problems of the prior art have been solved by the instant invention, which provides a process for the preparation of isophorone nitrile according to the following reaction:

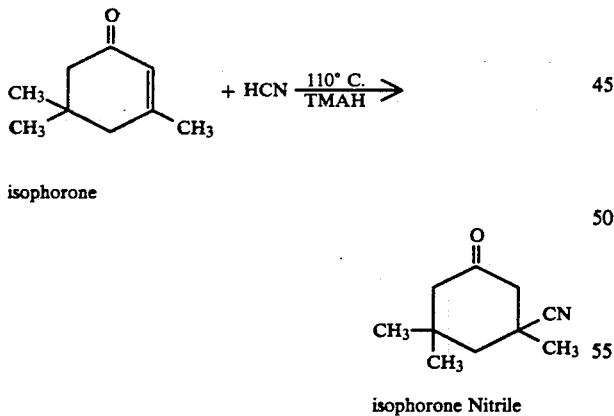

isophorone isophorone Nitrile

The isophorone nitrile is prepared by the Michael addition of HCN across the double bond of both the α and β isomers of isophorone. The instant process preferably utilizes a quaternary ammonium hydroxide as a catalyst. On a molar basis, tetramethyl, tetraethyl, and tetrabutyl ammonium hydroxides are equally effective catalysts. Because tetramethylammonium hydroxide (TMAH) has the lowest molecular weight and is also the least expensive quaternary ammonium hydroxide, TMAH is the preferred catalyst. The avoidance of the generation of large volumes of aqueous effluents can be accomplished by thermal destruction of the catalyst rather than aqueous washing to remove residual catalyst and residual HCN. The product of the thermal decomposition is trimethyl amine which can be scrubbed from the off-gases. Residual cyanide is removed by acidification of the crude product with an acid followed by sparging with an inert gas.

It is therefore an object of the invention to provide a process for the preparation of isophorone nitrile that uses an inexpensive, readily available catalyst.

It is a further object of the invention to prepare isophorone nitrile by a process that avoids generation of large volumes of aqueous effluents.

It is another object of the invention to provide a process for the preparation of isophorone nitrile that eliminates residual catalyst.

It is still another object of the invention to provide a process for the preparation of isophorone nitrile that eliminates residual cyanide.

It is a further object of the invention to provide a process for the preparation of isophorone nitrile that minimizes the generation of by-products.

DETAILED DESCRIPTION OF THE INVENTION

In preferred embodiments of the process of the instant invention, the quaternary ammonium catalyst is tetramethylammonium hydroxide (TMAH), preferably as a 25% solution in either water or methanol. The least expensive is the aqueous solution, although (in a subsequent step) the water will be stripped out of the product at the azeotropic composition 85% IPH/15% $H_2O$, which will then be a process waste stream. If this is undesirable, the methanolic version of the catalyst can be used. The methanol can be condensed and separated. The non-condensable trimethylamine can be sent to a water scrubber.

Quaternary ammonium hydroxides pyrolyze by the Hofmann Reaction.

TMAH thermally decomposes to trimethyl amine plus methanol:

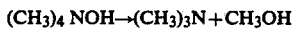

Tetraethylammonium hydroxide (TEAH) decomposes to triethyl amine plus ethanol:

Tetrabutylammonium hydroxide (TBAH) decomposes to tributyl amine plus butylene plus $H_2O$:

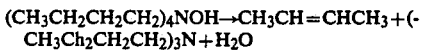

Figure 3:
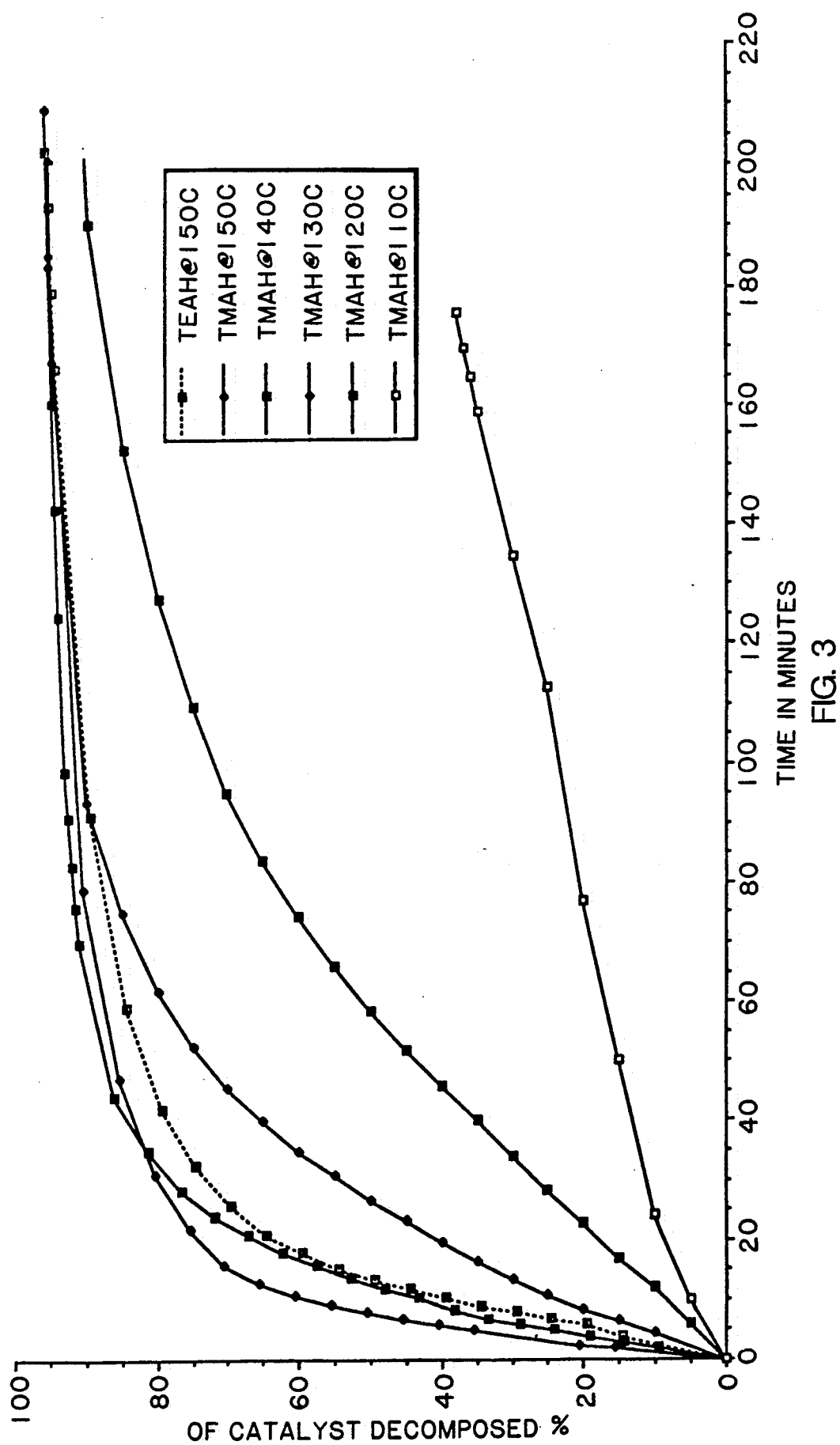
FIG. 3 is a graph showing the stability of quaternary ammonium hydroxide catalysts in isophorone at various temperatures.

These reactions can be applied in the instant process to remove the catalyst from IPN, thereby circumventing an aqueous wash and its concomitant generation of large volumes of effluent. FIG. 3 is a graphical illustration of the thermal decomposition of TMAH and tetraethylammonium hydroxide in an isophorone system at temperatures from 110° C. to 150° C. Most of the catalyst can be removed from the crude product at 140°-150° C. Prolonged heat up and hold periods at 150° C. during the catalyst destruction step create color bodies in the solids. Heating from 110° C. to 150° C. in a few minutes and holding at 150° C. or 140° C. for about an hour enabled white IPN to be isolated. Preferably, the thermal decomposition is carried out at about 140° C. for about 90 minutes, with sparging with an inert gas, preferably $N_2$, to remove volatile decomposition product. The sparging can be carried out anywhere from 100°-200° C., preferably about 110° C. However, if the temperature is raised to strip out IPH or distill IPN, the sparging can be carried out at that raised temperature (e.g., about 140°-150° C., or if a vacuum is present, as high as about 200° C). During sparging, isophorone/IPN solution is condensed and can be recycled to the next batch. Residual free cyanide is also destroyed in this step.

Alternatively, the catalyst can be removed by neutralization with an acid, such as phosphoric, nitric, or sulfuric acid, followed by removal of the resulting insoluble quaternary ammonium salts by filtration of the cooled isophorone solution. Typically the IPH/IPN solution is cooled to about 20°-30° C. for filtration of the TMAH salts.

The problem of cyanide contamination of all products, whether crude solutions or solids obtained by precipitation in a hydrocarbon and washing followed by vacuum drying to remove the hydrocarbon, or by vacuum distillation to isolate IPN itself, will now be discussed. It is believed that most of the residual HCN is free HCN or $CN^-$ rather than combined HCN, and probably exists in solution as the cyanide salt of TMAH. Neutralization with a strong mineral acid or an organic acid converts the cyanide to free HCN, which can then be eliminated by sparging with an inert gas, such as carbon dioxide or nitrogen, preferably nitrogen. Glacial acetic acid, phosphoric acid and sulfuric acid are suitable, with acetic acid being especially preferred. Phosphoric acid is the preferred mineral acid, as the phosphate anion has minimal impact on a subsequent hydrogenation step. The acid is preferably used in an amount equivalent to or greater than the residual catalyst on a molar basis. The sparging is carried out at a temperature of about 110° C. for about 1-2 hours. This procedure of mitigating cyanide contamination can be used in addition to or instead of the aforementioned catalyst pyrolysis. Specifically, if the catalyst is not destroyed by pyrolysis, acidification with an organic acid, preferably acetic acid, will result in the formation of a TMAH salt which is soluble in the IPN/isophorone solution, such as the acetate salt of TMAH. The salt does not have to be removed prior to the subsequent hydrogenation step, as it does not interfere in that hydrogenation. Since the resulting isophorone diamine (IPDA) must then be purified by distillation, the catalyst could be removed at that point. Alternatively, if the catalyst is not destroyed by pyrolysis but instead is neutralized by, e.g. phosphoric acid, the catalyst can be removed by filtration of the insoluble TMAH phosphate salt from the cooled isophorone/IPN solution.

A suitable minimum temperature for the reaction of isophorone to IPN is about 110° C.-115° C., preferably about 110° C. The sensitivity of the catalyst to temperature is a factor in selecting the minimum reaction temperature. At a mole ratio IPH:HCN:TMAH of 2.00:1.00:0.01 and a temperature of 110° C., the minimum HCN feed time is about 1 hour.

Isophorone is both a reactant and a solvent. To obtain high yields, isophorone must be used in stoichiometric excess to the HCN added. A ratio of 2 moles isophorone:1 mole HCN is preferred, but marginally higher yields are obtained with larger excesses of isophorone. As little as about 0.001 moles of catalyst (per mole HCN) can be used, although product yield may suffer. Preferably about 0.005 to 0.01, most preferably about 0.01 moles of catalyst are used. Larger amounts can be used, the limitation being cost.

Generally, the IPN product is needed free of isophorone. This can be accomplished by vacuum stripping off the isophorone to give a crude molten product which can then either be converted to a solid (e.g., on a chiller/flaker or a chilled belt) or dissolved in the solvent used for the subsequent hydrogenation to IPDA. Alternatively, the stripped melt can be vacuum distilled to produce a highly pure IPN.

In some manufacturing situations, the IPN dissolved in isophorone is the desired product form, e.g., as a 35% solution in isophorone. In this instance, the initial IPH charge is preferably increased to an amount sufficient to dilute the product solution to, e.g., 35% IPN. Since yield increases with higher IPH excesses, this procedure is preferred to adding IPH as a diluent to the product.

The generation of by-products can be mitigated by avoiding the addition of catalyst until the reaction temperature is reached, and by immediately starting the HCN feed once the catalyst is added. This procedure also results in increased yield of product.

Unless otherwise indicated, the apparatus used for the following Examples is illustrated in FIGS. I and II. The critical units are a one Liter Parr stirred autoclave and a Harvard Apparatus syringe pump equipped with a 100 ml stainless steel syringe. With this pump and syringe, the HCN could be delivered at precisely known and constant rates without any danger of loss of HCN.

EXAMPLE 1

Figure 1:
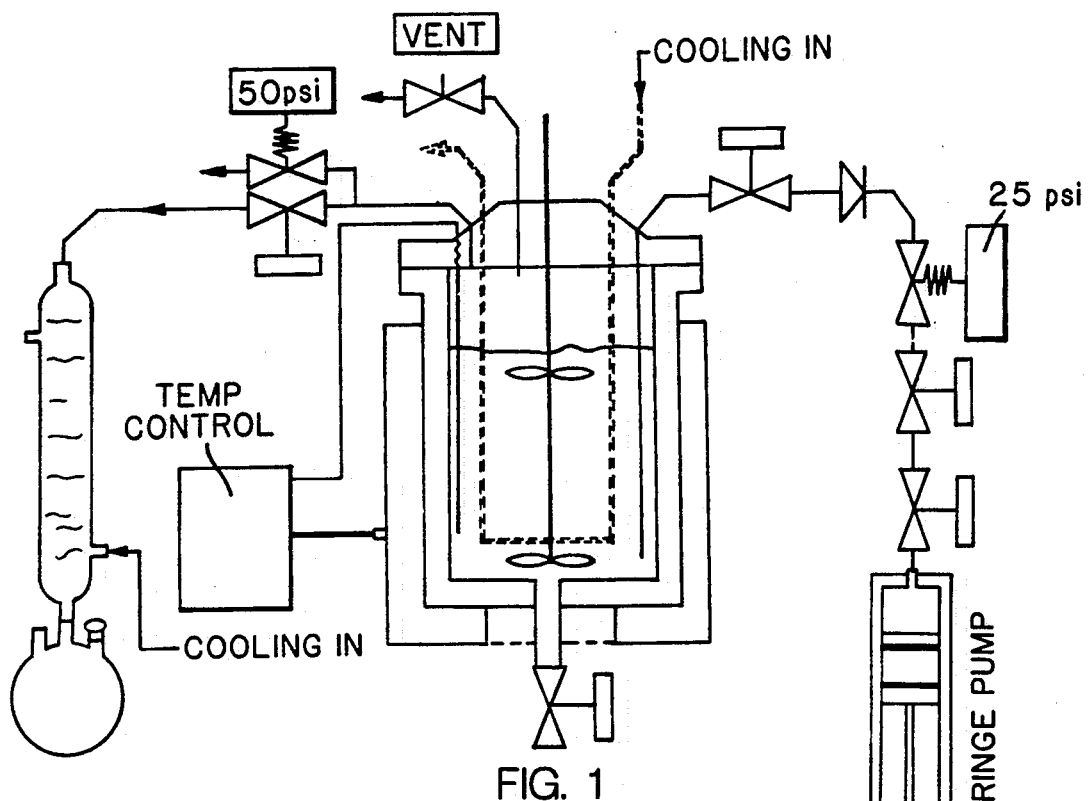
FIG. 1 illustrates laboratory apparatus used in the process of the instant invention.
Figure 2:
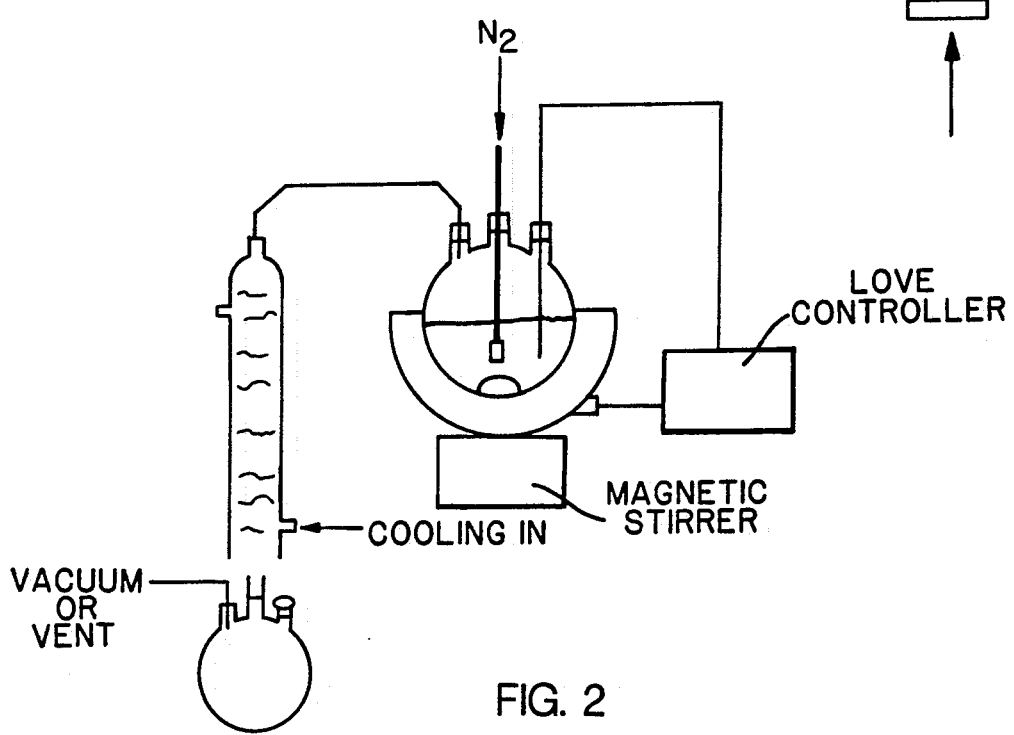
FIG. 2 illustrates laboratory sparge and stripping apparatus used in the process of the instant invention.

The apparatus is shown in FIG. 1. To the one liter stainless steel autoclave was charged 4.00 moles of isophrone. The head space was purged with nitrogen, then the autoclave was sealed. The temperature was raised to 80° C. and 0.02 moles of TMAH catalyst were added. The temperature was further increased to and held at 110° C. Two moles of anhydrous HCN were pumped into the isophrone by means of the stainless steel syringe pump at constant but different rates for several experiments. The batch was held for 1 hr at 110° C., sampled, and analyzed for %IPN and %HCN.

| Expt. No. | HCN Feed Time | % IPN Yield From HCN | ppm HCN at End of Feed |
|---|---|---|---|
| 1 | 2 hr | 88.4 | 501 |
| 2 | 1 hr | 95.2 | 406 |
| 3 | 30 min | 93.4 | 515 |
| 4 | 25 min | 74.2 | 1932 |
|  | after 1 hr hold | 85.4 | 310 |
| 5 | 1 hr | 94.3 | 541 |

EXAMPLE 2 - Thermal destruction of TMAH

IPN solutions in isophrone were prepared by the same procedure as in Example 1 but with a constant 1 hr HCN addition time. The solutions were heated to 120°, 130°, 140°, or 150° C. and sparged with $N_2$. The IPN-/isophrone solutions were analyzed at about 15 min time increments for residual TMAH by titration with standard HCl.

| Sparging Temperature | Minutes to Obtain Minimum Residual TMAH | ppm TMAH Initial | Final |
|---|---|---|---|
| 120° C. | 142 | 143 | 42 |
| 130° C. | 120 | 163 | 27 |
| 140° C. | 85 | 163 | 22 |
| 150° C. | 67 | 150 | 19 |

EXAMPLE 3 - Acidification/sparging to remove HCN

A solution of IPN in isophrone was prepared by the procedure of Example 1 using a 1 hr HCN feed and a 15 min hold period after the end of the HCN addition. 615 g was transferred to the sparging apparatus (FIG. 11). By titration, this solution contained 260 ppm of residual TMAH, or 17.5 milli moles. To this solution was added 2.7 g of 85% $H_3PO_4$, or 23.4 milli moles. The solution was heated to 110° C. and sparged with $N_2$. Samples were analyzed periodically for HCN.

| Before acidification | | 426 ppm HCN |
|---|---|---|
| After sparging for | 30 min | 299 |
| | 60 | 49 |
| | 90 | 0 |

EXAMPLE 4

Four batches of IPN solution in isophrone were prepared in a 30 gallon stainless steel reactor fitted with a reflux condenser. To the reactor was charged 172 lb (1.22 lb moles) of isophrone via vacuum. The vacuum was then broken by bleeding in $N_2$ to 0 psig. The isophrone was heated to 110° C. and 1.48 or 1.11 lb of 25% aqueous TMAH (0.004 or 0.003 lb moles) was added. Addition of 11.0 lb of HCN (0.41 lb moles) was started immediately and finished about 1 hr later. During the HCN addition the batch temperature was maintained at 110°-115° C. The batch was then sampled and analyzed for IPN, TMAH, and HCN. Glacial acetic acid was added and the batch sparged with $N_2$ at 110°-115° C. for 30 min, at which time no HCN could be detected in any of the four batches. The solution was then cooled to about 30° C. and diluted with isophrone to about 35% IPN.

| Run No. | Yield (%) After HCN Feed | Yield (%) Final Product | TMAH Catalyst mole/mole of HCN | Glacial Acetic Acid Added lb | Glacial Acetic Acid Added Mole/Mole of TMAH Charged | ppm HCN After HCN Feed |
|---|---|---|---|---|---|---|
| 1 | 100.4 | 98.5 | 0.01 | 0.363 | 1.51 | 235 |
| 2 | 99.7 | 97.2 | 0.01 | 0.290 | 1.21 | n.d.* |
| 3 | 99.2 | 97.2 | 0.0075 | 0.220 | 1.22 | n.d.* |
| 4 | 97.3 | 93.4 | 0.0075 | 0.220 | 1.22 | n.d.* |

*Not determined

What is claimed:

1. A process for the preparation of isophorone nitrile comprising:
   a reacting isophorone with hydrogen cyanide in the presence of a quaternary ammonium hydroxide catalyst selected from the group consisting of tetramethylammonium hydroxide, tetraethylammonium hydroxide and tetrabutylammonium hydroxide in a mole ratio of isophorone: hydrogen cyanide: catalyst of about 2.00-3.00: 1.00: 0.005-0.01 and at a temperature of at least about 110° C.
   b adjusting the temperature of the resulting mixture to about 110° C. -150° C. to decompose remaining catalyst;
   c sparging with an inert gas at a temperature of about 100° C.-200° C. to remove the resulting quaternary ammonium catalyst decomposition product;
   d acidifying the mixture with an acid selected from the group consisting of acetic acid, sulfuric acid and phosphoric acid, and sparging with an inert gas to eliminate residual cyanide.

2. The process according to claim 1 wherein the temperature achieved in step b is about 140° C. and is held for about one hour.

3. The process according to claim 1 wherein the acid is acetic.

4. The process according to claims 1 wherein said acid is sulfuric, thereby forming the sulfate salt of said catalyst, and further comprising the step of removing said salt by filtration.

5. The process according to claim 1 wherein said acid is phosphoric, thereby forming the phosphate salt of said catalyst, and further comprising the step of removing said salt by filtration.

6. The process according to claim 1 wherein the quaternary ammonium catalyst comprises tetramethylammonium hydroxide.

7. The process according to claim 1 wherein the quaternary ammonium catalyst decomposition product comprises trimethylamine.

8. The process according to claim 1 wherein the catalyst in step a is added after the reaction temperature is reached.

9. The process according to claim 8 wherein the hydrogen cyanide in step a is added after said catalyst addition.

10. The process according to claim 1 wherein the inert gas is nitrogen.

11. A process for the preparation of isophorone nitrile comprising:
    a reacting isophorone with hydrogen cyanide in the presence of a quaternary ammonium hydroxide catalyst selected from the group consisting of tetramethylammonium hydroxide, tetraethylammonium hydroxide and tetrabutylammonium hydroxide in a mole ratio of isophorone: hydrogen cyanide: catalyst of about 2.00-3.00: 1.00: 0.005-0.01 and at a temperature of at least about 110° C.;
    b acidifying the resulting reaction mixture with an acid selected from the group consisting of acetic acid, sulfuric acid, nitric acid and phosphoric acid;
    c sparging the mixture at a temperature of about 110° C. with an inert gas.

12. The process according to claim 11 wherein the acid is sulfuric, thereby forming the sulfate salt of said catalyst, and further comprising removing said salt by filtration.

13. The process according to claim 11 wherein the acid is phosphoric, thereby forming the phosphate salt of said catalyst, and further comprising removing said salt by filtration.

14. The process according to claim 11 wherein the quaternary ammonium catalyst comprises tetramethylammonium hydroxide.

15. The process according to claim 11 wherein the catalyst in step a is added after the reaction temperature is reached.

16. The process according to claim 15 wherein the hydrogen cyanide in step a is added after said catalyst addition.

17. The process according to claim 11 wherein the inert gas is nitrogen.

* * * * *